United States Patent
Rabie

(10) Patent No.: US 9,914,154 B2
(45) Date of Patent: Mar. 13, 2018

(54) MULTI-BLADE RAZOR CARTRIDGE CLEANER

(71) Applicant: Frederick Firouz Rabie, North Potomac, MD (US)

(72) Inventor: Frederick Firouz Rabie, North Potomac, MD (US)

( * ) Notice: Subject to any disclaimer, the term of this patent is extended or adjusted under 35 U.S.C. 154(b) by 0 days.

(21) Appl. No.: 14/545,741

(22) Filed: Jun. 12, 2015

(65) Prior Publication Data

US 2017/0197234 A1    Jul. 13, 2017

(51) Int. Cl.
*B08B 3/02* (2006.01)
*B26B 21/40* (2006.01)

(52) U.S. Cl.
CPC ............... *B08B 3/02* (2013.01); *B26B 21/40* (2013.01)

(58) Field of Classification Search
CPC .................................. B26B 21/40; B08B 3/02
See application file for complete search history.

(56) References Cited

U.S. PATENT DOCUMENTS

| | | | | |
|---|---|---|---|---|
| 4,838,949 A * | 6/1989 | Dugrot | ................... | A45D 27/46 134/166 R |
| 5,649,556 A * | 7/1997 | Braun | ................... | A45D 27/46 134/111 |
| 5,711,328 A * | 1/1998 | Braun | ................... | A45D 27/46 134/111 |
| 6,371,136 B1 * | 4/2002 | Hoser | ................... | A45D 27/46 134/111 |
| 6,626,194 B2 * | 9/2003 | Wong | ................... | A45D 27/46 134/102.1 |
| 7,409,960 B2 * | 8/2008 | Hoser | ................... | A45D 27/46 134/109 |
| 2004/0194326 A1 * | 10/2004 | Kappes | ................... | A45D 27/46 30/537 |
| 2005/0005453 A1 * | 1/2005 | Egeresi | ................... | B26B 19/34 30/34.1 |
| 2006/0053642 A1 * | 3/2006 | Kappes | ................... | A45D 27/46 30/537 |
| 2006/0283487 A1 * | 12/2006 | Grabowski | ............... | B08B 3/02 134/184 |
| 2013/0180117 A1 * | 7/2013 | Hobson, Sr. | ........ | B26B 21/4068 30/346.53 |
| 2014/0208601 A1 * | 7/2014 | Battin | ................... | A45D 27/46 30/538 |

* cited by examiner

*Primary Examiner* — Michael Barr
*Assistant Examiner* — Benjamin L Osterhout
(74) *Attorney, Agent, or Firm* — Kilpatrick Townsend & Stockton LLP

(57) ABSTRACT

A multi-blade razor cartridge cleaner system is a device that cleans between the blades of razors with a jet-spray of water to remove the hair and soap that gets trapped during every few passes of the razor across the skin surface. The razor is placed within a slot on top of the cartridge cleaner housing and a switch is activated to jet-spray the razor cartridge blades clean.

20 Claims, 5 Drawing Sheets

MULTI-BLADE RAZOR CARTRIDGE CLEANER

CROSS-REFERENCE TO RELATED APPLICATION

The present application is related to and claims priority from prior provisional application Ser. No. 61/998,326, filed Jun. 24, 2014 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of razor cleaning devices and more specifically relates to a multi-blade razor cartridge cleaner.

2. Description of the Related Art

In modern society, clean shaven faces or at least neatly trimmed beards or mustaches are the acceptable standard for men. For women, clean shaven legs and underarms are the accepted standard. There are different methods that hair can be temporarily removed such as electric razors, chemical creams, straight razors, and disposable razors having multiple blades. Disposable razors or razors with disposable cartridges are the most commonly used methods for shaving. Shaving with a razor can arguably provide the smoothest shave and may be why it is the most popular method, but can create its own set of inconveniences. For instance, a multi-blade razor cartridge provides a smooth comfortable shave, but hair and shaving creams tend to get 'jammed' between the individual razor blades in the cartridge until the razor is loaded and will not cut hair efficiently until the blades are cleaned. Typically, vigorously shaking the razor back and forth in a sink full of water or holding the razor under a fast miming water faucet gets cleans most of the hair and soap from between the blades. Often, the razor needs to be struck against the edge of the sink to get the debris out. If the soap and hair is left between the blades to dry, the life of the cartridge will be greatly reduced. A convenient solution is necessary.

Ideally, a razor cleaner should provide convenience and effectiveness, and yet, would operate reliably and be manufactured at a modest expense. Thus, a need exists for a reliable multi-blade razor cartridge cleaner to avoid the above-mentioned problems.

BRIEF SUMMARY OF THE INVENTION

In view of the foregoing disadvantages inherent in the known razor cleaning devices art, the present invention provides a novel multi-blade razor cartridge cleaner. The general purpose of the present invention, which will be described subsequently in greater detail is to provide convenience and razor cleaning effectiveness.

The present invention, multi-blade razor cartridge cleaner systems, as disclosed herein, preferably is a device that cleans between the blades of razors with a jet-spray of water to remove the hair and soap that gets trapped during every few passes of the razor across the skin surface. The razor is placed within a slot on top of the cartridge cleaner housing beneath the cover and a switch operated to activate the jet-spray. The cartridge cleaner assembly is useful for cleaning the debris from between the multiple razor blades of the razor cartridge and extending a life span of the razors in the razor cartridge. In a preferred embodiment, the cartridge cleaner assembly may comprise a cartridge cleaner assembly having a clean water tank, a pump, a cartridge cleaner housing with a top side, a bottom side, a proximate end, and a distal end, an inner volume, a razor rest, a cleaning chamber having a spray cover, at least one jet-spray nozzle, and a disposal tank.

The multi-blade razor cartridge cleaner system is comprised of a cartridge cleaning assembly, which has various similar embodiments. Each embodiment of the cartridge cleaner assembly is in operative communication with the clean water tank, the pump, the cartridge cleaner housing, the razor rest, the cleaning chamber having a spray cover, the plurality of jet-spray nozzles, and the disposal tank. The clean water tank, the pump, and the disposal tank may be removable located in the cartridge cleaner housing in a preferred embodiment. The clean water tank preferably is located in the proximate end of the cartridge cleaner housing within the inner volume and is operatively coupled to the pump, also being located interiorly of the cartridge cleaner housing. The clean water tank preferably is able to slide into and out of the cartridge cleaner housing for filling, or in some embodiments, may comprise a fill aperture accessible from the outside of the cartridge cleaner housing. The clean water tank may comprise different shapes in different embodiments, but is preferably somewhat L-shaped with a connection point to the pump at the lowermost end of the tank.

In another embodiment, the clean water tank is exteriorly located and attachable to, and detachable from the cartridge cleaner housing. The pump preferably comprises a miniature positive displacement type pump, but may comprise other types in alternate embodiments that are capable of developing a forceful enough jet-spray to clean between the blades of the razor. The pump may also be operable with a 12 volt DC current motor in one embodiment and may also be operable with a 110-volt or 220-volt AC current motor in another embodiment. The cartridge cleaning assembly is not defined by or restricted to a particular voltage motor for the pump, for instance, the cartridge cleaning assembly may be operable by 1.5 volts DC using double A or triple A batteries in parallel, or may be operable by 3, 6, or 9 volts using double A or triple A batteries in series or a 9 volt DC battery. The batteries may be rechargeable with any of the above-mentioned voltages or may be disposable.

The cartridge cleaning assembly has an inner volume that may house the pump, depending on embodiment, which is operatively coupled to at least one jet-spray nozzle. The jet-spray nozzle sprays in a fan shaped pattern and or in a stream having one or more jet-spray nozzle. In another embodiment, the pump may be exteriorly attachable and detachable to the cartridge cleaner housing. In one embodiment, the cartridge cleaner housing may comprise two halves (shells) that snap together, and un-snap to expose the components of the inner volume such as the clean water tank, the pump, and the disposal tank. The two halves may fasten together using screws in addition to snapping together. The cartridge cleaner housing may have a slide door, in another embodiment, for accessing the inner volume instead of having two halves. In a preferred embodiment, the housing has enclosed sides with openings at the proximate end and distal end for sliding the clean water tank and the disposal tank respectively.

In a preferred embodiment, the spray cover is substantially rectangular shaped with one open side and either sets securely atop the cartridge cleaner housing or snaps into place. In an alternate embodiment, the spray cover may be spring loaded so that it is closed when in a relaxed state and spring tensioned in the open position. In an alternate embodiment, the spray cover may also have a slot in the bottom edge over the razor rest so that the handle of the razor is able to extend through to the exterior of the spray cover. The razor rest is located on the topside of the cartridge cleaning housing such that a razor placed therein is nestably situated within the razor rest beneath the spray cover.

The cartridge cleaning housing may have a shape selected from the group of: square, rectangular, oblong, circular, and L-shaped. The cleaning chamber is located near the distal end of the top side of the cartridge cleaner housing. The jet-spray nozzle(s) extends through the sidewall of the cleaning chamber and is able to be upwardly positioned to jet-spray debris from between the downward facing razor blades of the razor cartridge, or angled to any degree or placed in any position to direct the jet-spray in any direction. A downwardly extending drain tube from the bottom of the cleaning chamber extends into the disposal tank. The disposal tank is slideably located beneath the cleaning chamber such that the spray-water from the jet-spray nozzle(s) drain downward into the disposal tank. The disposal tank may be exteriorly attachable and detachable to the cartridge cleaner housing in some embodiments. The disposal tank may have a drain plug in one embodiment, or may be detachable from the exterior of the cartridge cleaner assembly, or slideably removable from the interior of the housing in other embodiments, so that the user can empty the tank when it gets full.

The multi-blade razor cartridge cleaner system may further comprise a kit including at least one assembled cartridge cleaner assembly having a clean water tank, a pump, a cartridge cleaner housing having a razor rest, a cleaning chamber having a spray cover, a plurality of jet-spray nozzles, a disposal tank, and at least one set of user instructions.

A method of using the multi-blade razor cartridge cleaner system may comprise the steps of; filling the clean water tank with tap water; beginning the shaving process; placing a razor in the razor slot in the top side of the cartridge cleaner housing; activating the jet-spray to clean the razor as needed; and removing and storing the razor.

The present invention holds significant improvements and serves as a multi-blade razor cartridge cleaner. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, multi-blade razor cartridge cleaner, constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to a razor cleaning device and more particularly to a multi-blade razor cartridge cleaner system as used to improve the convenience and effectiveness of cleaning a multi-blade razor. The multi-blade razor cartridge cleaner system is described in greater detail in the following exemplary figures.

Figure 1:
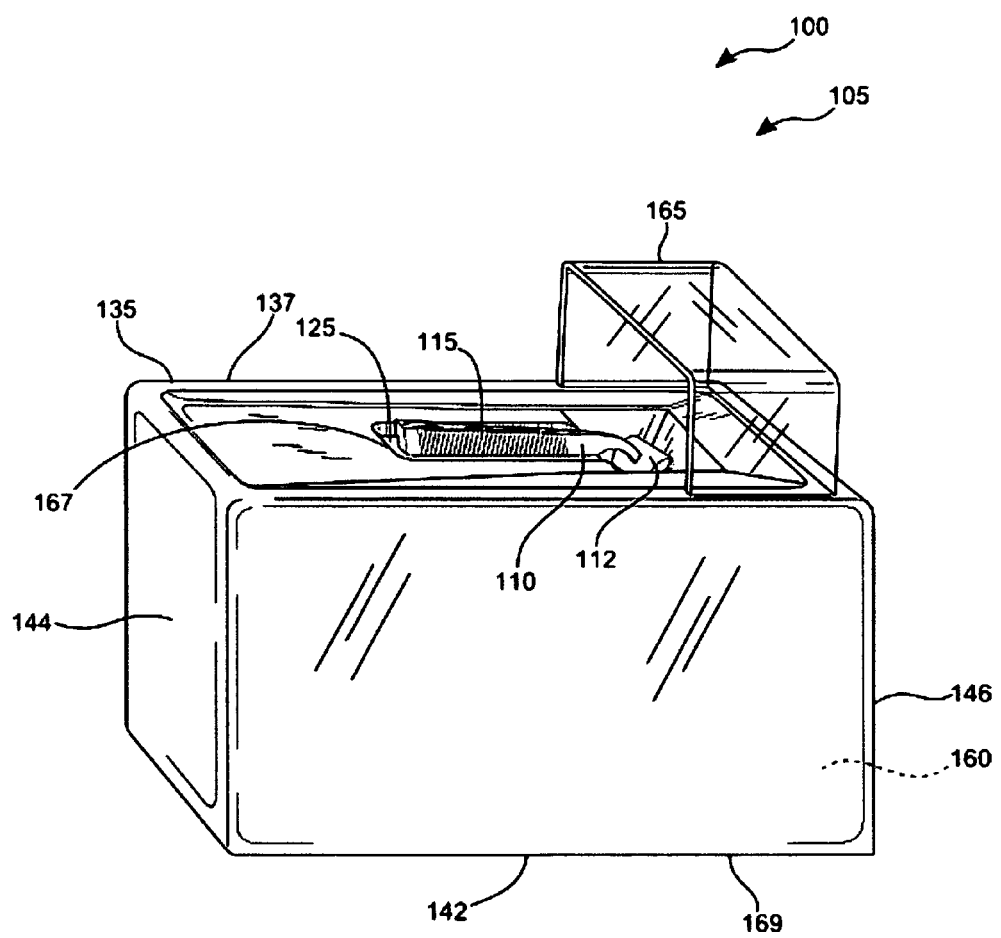
FIG. 1 shows a perspective view illustrating a multi-blade razor cartridge cleaner system according to an embodiment of the present invention.

Referring to the drawings by numerals of reference, there is shown in FIG. 1, a perspective view illustrating multi-blade razor cartridge cleaner system 100 according to an embodiment of the present invention.

Multi-blade razor cartridge cleaner systems 100 preferably is a device that cleans between the blades of razor(s) 110 with jet-spray 200 of water to remove the hair and soap that gets trapped during every few passes of razor(s) 110 across the skin surface. Cartridge cleaner assembly 105 is useful for cleaning the debris from between the multiple razor blades of razor cartridge 112 and extending the life span of the blades in razor cartridge 112. Razor(s) 110 is/are placed within razor rest 125 on top side 137 of cartridge cleaner housing 135 and beneath cover 165 and a switch activated to jet-spray 200 razor cartridge for cleaning. In a preferred embodiment, multi-blade razor cartridge cleaner systems 100 may comprise cartridge cleaner assembly 105 having clean water tank 130, pump 150, cartridge cleaner housing 135 with top side 137, bottom side 142, proximate end 144, and distal end 146, inner volume 148, razor rest 125, cleaning chamber 160 having spray cover 165 and at least one jet-spray nozzle 170, and disposal tank 180. Spray cover 165 may also have an open end for placing razor(s) 110 therein.

Figure 2:
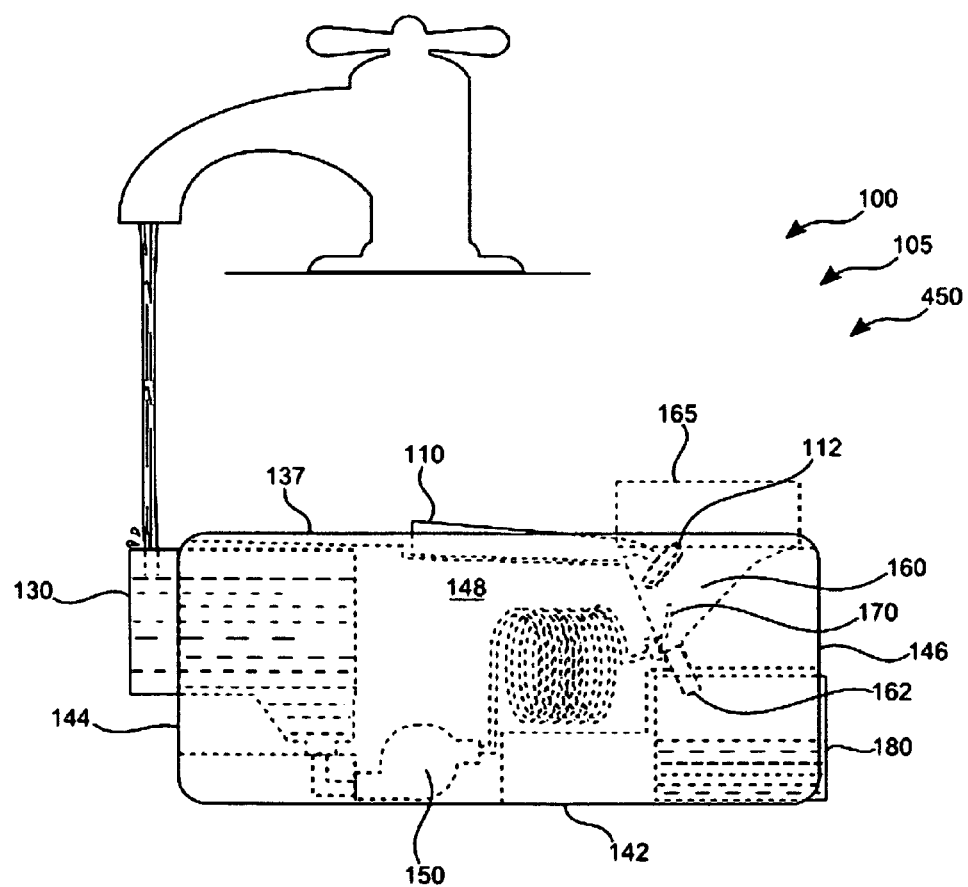
FIG. 2 is a side view illustrating the multi-blade razor cartridge cleaner system according to an embodiment of the present invention of FIG. 1.

Referring now to FIG. 2, a side view illustrating multi-blade razor cartridge cleaner system 100 according to an embodiment of the present invention of FIG. 1.

Multi-blade razor cartridge cleaner systems 100 is preferably comprised of cartridge cleaner assembly 105 which has various similar embodiments suitable for convenient use by consumers. Each embodiment of cartridge cleaner assembly 105, includes clean water tank 130, pump 150, cartridge cleaner housing 135, razor rest 125, cleaning chamber 160 having spray cover 165, a plurality of jet-spray nozzle(s) 170, and disposal tank 180 and is structured and arranged to be operatively functional to clean razor cartridge(s) 112.

Clean water tank 130, pump 150, and disposal tank 180 may be located within cartridge cleaner housing 135 in a preferred embodiment. Clean water tank 130 preferably is located at proximate end 144 within inner volume 148 of cartridge cleaner housing 135 and is operatively coupled to pump 150, which is also located interiorly of cartridge cleaner housing 135. Cleaning chamber 160 is located near distal end 146 of top side 137 of cartridge cleaner housing 135. Spray cover 165 is positioned over razor(s) 110 placed on razor rest 125, cleaning chamber 160, and jet-spray nozzle(s) 170, to prevent the spray-water from exteriorly spraying from cartridge cleaner housing 135. Jet-spray nozzle(s) 170 extends through the sidewall of cleaning chamber 160 and may be upwardly positioned to jet-spray 200 debris from between the downward facing razor blades of the razor cartridge(s) 112, but jet-spray nozzle(s) 170 may be positioned at any angle and spray in any direction as desired by the user.

In another embodiment, clean water tank 130 is exteriorly located and attachable-to, and detachable from cartridge cleaner housing 135. Pump 150 preferably comprises a miniature positive displacement type pump 150, but may comprise other types in alternate embodiments that are capable of developing a forceful enough jet-spray 200 to clean between the blades of razor(s) 110. pump 150 may also be operable with a 12 volt dc current motor in one embodiment and may also be operable with a 110 or 220 volt ac current motor in other embodiments. In another embodiment, pump 150 may be exteriorly attachable and detachable to cartridge cleaner housing 135. Cartridge cleaner assembly 105 is not defined by or restricted to a particular voltage, motor for pump 150, for instance, cartridge cleaner assembly 105 may be operable by 1.5 volts dc using double a or triple a batteries in parallel, or may be operable by 3, 6, or 9 volts using double a or triple a batteries in series.

Figure 3:
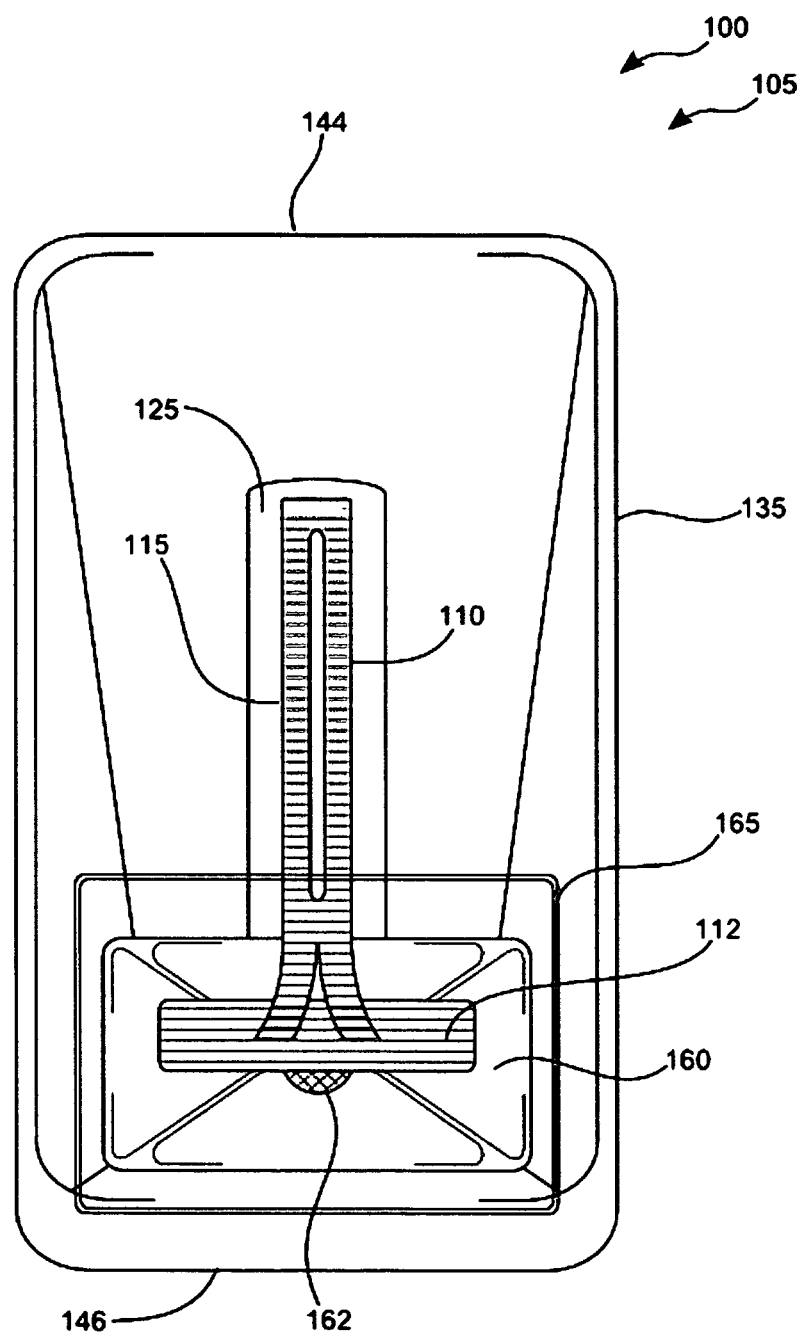
FIG. 3 is a top view illustrating the multi-blade razor cartridge cleaner system according to an embodiment of the present invention of FIG. 1.

Referring now to FIG. 3, a top view illustrating multi-blade razor cartridge cleaner system 100 according to an embodiment of the present invention of FIG. 1.

Clean water tank 130 may comprise a fill aperture accessible from the outside of cartridge cleaner housing 135 in an alternate embodiment, but in a preferred embodiment, may be removable from cartridge cleaner housing 135 and fillable from a sink faucet. Cartridge cleaner assembly 105 has inner volume 148 that may house pump 150, depending on embodiment, which is operatively coupled to at least one jet-spray nozzle(s) 170. Jet-spray nozzle(s) 170 preferably sprays in a fan shaped pattern and or in a stream in embodiments with one or more jet-spray nozzle(s) 170. Razor rest 125 is located on top side 137 of cartridge cleaner housing 135 such that razor(s) 110 placed therein is nestably situated within razor rest 125.

Figure 4:
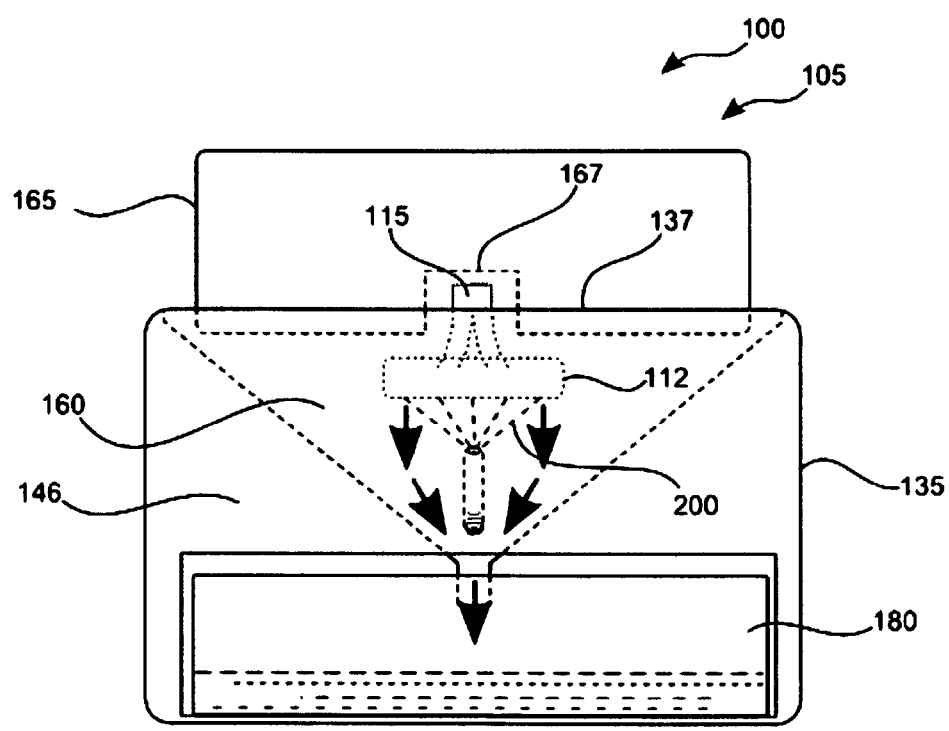
FIG. 4 is a front view illustrating the multi-blade razor cartridge cleaner system according to an embodiment of the present invention of FIG. 1.

Referring now to FIG. 4, showing a front view illustrating multi-blade razor cartridge cleaner system 100 according to an embodiment of the present invention of FIG. 1.

In one embodiment, cartridge cleaner housing 135 may comprise two halves that snap together, and un-snap to expose the components of inner volume 148 such as clean water tank 130, pump 150, and disposal tank 180. The two halves may fasten together using screws in addition to snapping together. Cartridge cleaner housing 135 may have a slide door, in another embodiment, for accessing inner volume 148 instead of having two halves. Cartridge cleaner housing 135 may have a shape selected from the group of: square, rectangular, oblong, circular, and L-shaped. A downwardly extending drain tube 162 attaches to the bottom of cleaning chamber 160 with disposal tank 180 located beneath. Disposal tank 180 is located beneath cleaning chamber 160 such that the spray-water from jet-spray nozzle(s) 170 drain downward into disposal tank 180. Disposal tank 180 may be slideably removable in a preferred embodiment, or may be exteriorly attachable and detachable to cartridge cleaner housing 135 in some embodiments. Disposal tank 180 may have a drain plug in one embodiment, or may be detachable from the exterior of cartridge cleaner assembly 105, or may be able to be lifted from inner volume 148 of cartridge cleaner housing 135 in other embodiments, so that the user can empty disposal tank 180 when it gets full or after use.

Multi-blade razor cartridge cleaner system 100 may be sold as kit 450 comprising the following parts: at least one assembled cartridge cleaner assembly 105 having clean water tank 130, pump 150, cartridge cleaner housing 135 having razor rest 125, cleaning chamber 160 having spray cover 165, a plurality of jet-spray nozzle(s) 170, and disposal tank 180; and at least one set of user instructions. The kit has instructions such that functional relationships are detailed in relation to the structure of the invention (such that the invention can be used, maintained, or the like in a preferred manner). Multi-blade razor cartridge cleaner 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different housing/water draining combinations, parts may be sold separately, etc., may be sufficient.

Figure 5:
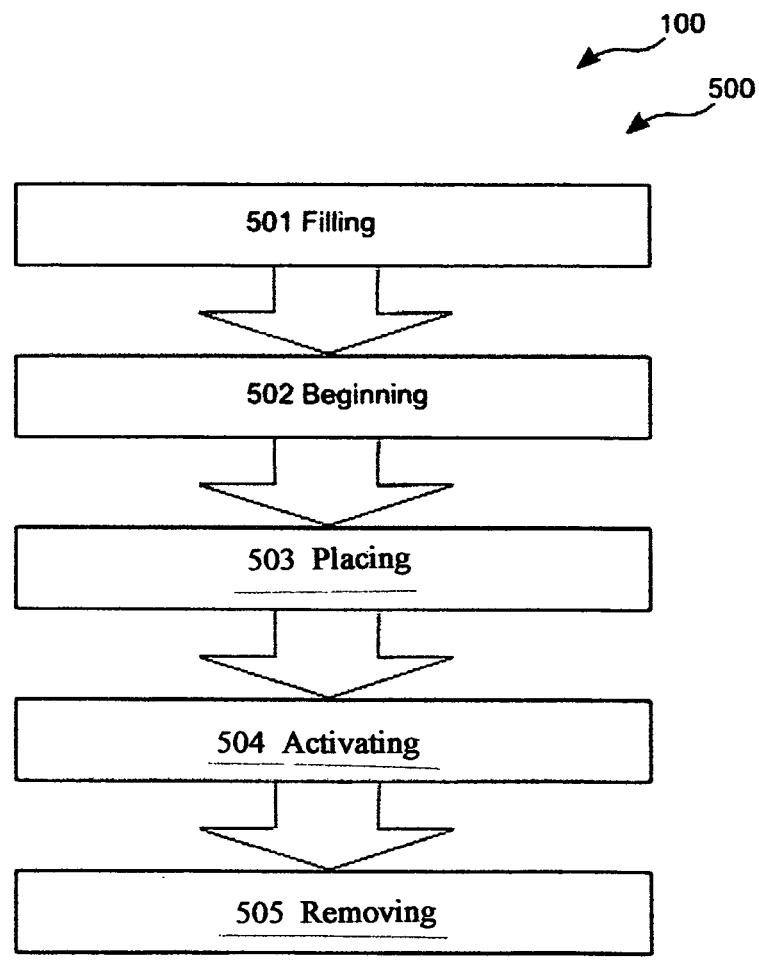
FIG. 5 is a flowchart illustrating a method of use for the multi-blade razor cartridge cleaner system according to an embodiment of the present invention of FIGS. 1-4.

Referring now to FIG. 5, showing a flowchart illustrating method of use 500 for multi-blade razor cartridge cleaner 100 according to an embodiment of the present invention of FIGS. 1-4.

Method of use 500 for multi-blade razor cartridge cleaner systems 100 may comprise the steps of step one 501 filling clean water tank 130 with tap water; step two 502 beginning the shaving process; step three 503 placing razor(s) 110 in razor rest 125 on top side 137 of cartridge cleaner housing 135; step four 504 activating the jet-spray 200 to clean razor(s) 110 as needed; and step five 505 removing and storing razor(s) 110.

It should be noted that step 501 is an optional step and may not be implemented in all cases. Optional steps of method 500 are illustrated using dotted lines in FIG. 5 so as to distinguish them from the other steps of method 500.

It should be noted that the steps described in the method of use can be carried out in many different orders according to user preference. The use of "step of" should not be interpreted as "step for", in the claims herein and is not intended to invoke the provisions of 35 U.S.C. §112, ¶6.

Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A multiple blade razor cartridge cleaner system comprising: a cartridge cleaner assembly comprising;
    a clean water tank;
    a pump;
    a cartridge cleaner housing having a top side, a bottom side, a proximate end, and a distal end and an inner volume;
    a razor rest;
    a cleaning chamber having a spray cover; at least one jet-spray nozzle; and a disposal tank;
    wherein said multiple blade razor cartridge cleaner system comprises said cartridge-cleaning assembly;
    wherein said cartridge cleaner assembly is in operative communication with said clean water tank, said pump, said cartridge cleaner housing, said razor rest, said cleaning chamber having said spray cover, said at least one jet-spray nozzle, and said disposal tank;
    wherein said clean water tank is located at said proximate end within said inner volume of said cartridge cleaner housing and is operatively coupled to said pump;
    wherein said pump is located within said inner volume of said cartridge cleaner housing and is operatively coupled to said at least one jet-spray nozzle;
    wherein said razor rest is located on said top side of said cartridge cleaner housing such that a razor placed therein is nestably situated within said razor rest;
    wherein said cleaning chamber is located near said distal end of said cartridge cleaner housing;
    wherein said spray cover is positioned to cover a placed said razor in said razor rest, said cleaning chamber, and said at least one jet-spray nozzle, to prevent a spray-water from exteriorly spraying from said cartridge cleaner housing;
    wherein said at least one jet-spray nozzle extends through a sidewall of said cleaning chamber and into said cleaning chamber and is upwardly and rotatably positioned to jet-spray a debris from between said multiple blades of said razor cartridge;
    wherein said disposal tank is located beneath said cleaning chamber such that said spray-water from said at least one jet-spray nozzle drains downward into said disposal tank; and
    wherein said cartridge cleaner assembly is useful for cleaning said debris from between said multiple blades of said razor cartridge and extending a life span of said blades of said razor cartridge.

2. The multiple blade razor cartridge cleaner system of claim 1 wherein said cartridge cleaner housing comprises a drain tube extending downwardly from said cleaning chamber into said disposal tank.

3. The multiple blade razor cartridge cleaner system of claim 1 wherein said at least one jet-spray nozzle is coupled to said pump via a hose.

4. The multiple blade razor cartridge cleaner system of claim 1 wherein said cartridge cleaner housing comprises a shape selected from the group of: square, rectangular, oblong, circular, and L-shaped.

5. The multiple blade razor cartridge cleaner system of claim 4 wherein said cartridge cleaner housing comprises two halves.

6. The multiple blade razor cartridge cleaner system of claim 4 wherein said clean water tank and said disposal tank are slideably removable from said proximate end and said distal end of said cartridge cleaner housing respectively.

7. The multiple blade razor cartridge cleaner system of claim 1 wherein said pump comprises a positive displacement pump.

8. The multiple blade razor cartridge cleaner system of claim 7 wherein said positive displacement pump is operable via 12 volt DC current.

9. The multiple blade razor cartridge cleaner system of claim 7 wherein said positive displacement pump is operable via 110 volts AC current.

10. The multiple blade razor cartridge cleaner system of claim 9 wherein said positive displacement pump is exteriorly attachable and alternately detachable to said cartridge cleaner housing.

11. The multiple blade razor cartridge cleaner system of claim 1 wherein said disposal tank comprises a drain plug.

12. The multiple blade razor cartridge cleaner system of claim 11 wherein said disposal tank is exteriorly attachable and alternately detachable to said cartridge cleaner housing.

13. The multiple blade razor cartridge cleaner system of claim 1 wherein said clean water tank comprises a fill aperture.

14. The multiple blade razor cartridge cleaner system of claim 13 wherein said clean water tank is exteriorly attachable and alternately detachable to said cartridge cleaner housing.

15. The multiple blade razor cartridge cleaner system of claim 13 wherein said clean water tank, said pump, and said disposal tank are interiorly located in said cartridge cleaner housing.

16. The multiple blade razor cartridge cleaner system of claim 1 wherein said spray cover is securely set over said cleaning chamber to prevent spray water from spraying outwardly from said cartridge cleaner housing.

17. The multiple blade razor cartridge cleaner system of claim 16 wherein said spray cover comprises a slot such that a handle of said razor is able to extend therethrough to an exterior of said spray cover.

18. A multiple blade razor cartridge cleaner system comprising:
    a cartridge cleaner assembly comprising;
    a clean water tank;
    a pump;
    a cartridge cleaner housing having a top side, a bottom side, a proximate end, and a distal end and an inner volume;
    a razor rest;

a cleaning chamber having a spray cover; at least one jet-spray nozzle; and a disposal tank;

wherein said multiple blade razor cartridge cleaner system comprises said cartridge-cleaning assembly;

wherein said cartridge cleaner assembly is in operative communication with said clean water tank, said pump, said cartridge cleaner housing, said razor rest, said cleaning chamber having said spray cover, said at least one jet-spray nozzle, and said disposal tank;

wherein said clean water tank, said pump, and said disposal tank are interiorly located in said cartridge cleaner housing;

wherein said clean water tank is located at said proximate end within said inner volume of said cartridge cleaner housing and is operatively coupled to said pump;

wherein said clean water tank and said disposal tank are slideably removable from said proximate end and said distal end of said cartridge cleaner housing respectively;

wherein said clean water tank comprises a fill aperture;

wherein said clean water tank is exteriorly attachable and alternately detachable to said cartridge cleaner housing;

wherein said pump comprises a positive displacement pump;

wherein said pump is operable via 12 volt DC current;

Wherein said pump is operable via 1.5 volt DC current;

wherein said pump is operable via 3 volt DC current;

wherein said pump is operable via 6 volt DC current;

wherein said pump is operable via 9 volt DC current;

wherein said pump is operable via rechargeable battery;

wherein said pump is operable via 110 volts AC current;

wherein said pump is operable via 220 volts AC current;

wherein said pump is located within said inner volume of said cartridge cleaner housing and is operatively coupled to said at least one jet-spray nozzle;

wherein said pump is exteriorly attachable and alternately detachable to said cartridge cleaner housing;

wherein said cartridge cleaner housing comprises two halves such that an interiorly located said clean water tank, said pump, and said disposal tank are each able to be accessed;

wherein said cartridge cleaner housing comprises a slide door for accessing an interiorly located said clean water tank, said pump, and said disposal tank such that each are able to be accessed;

wherein said spray cover is securely set over said cleaning chamber to prevent spray water from spraying outwardly from said cartridge cleaner housing;

wherein said spray cover comprises a slot such that a handle of said razor is able to extend there through to an exterior of said spray cover;

wherein said at least one jet-spray nozzle is coupled to said pump via a hose;

wherein said razor rest is located on said top side of said cartridge cleaner housing such that a razor placed therein is nestably situated within said razor rest;

wherein said cartridge cleaner housing comprises a shape selected from the group of: square, rectangular, oblong, circular, and L-shaped;

wherein said cleaning chamber is located near said distal end of cartridge cleaner housing;

wherein said spray cover is positioned to cover a placed said razor in said razor rest, said cleaning chamber, and said at least one jet-spray nozzle, to prevent a spray-water from exteriorly spraying from said cartridge cleaner housing;

wherein said at least one jet-spray nozzle extends through a sidewall of said cleaning chamber and into said cleaning chamber and is upwardly positioned to jet-spray a debris from between said multiple blades of said razor cartridge;

wherein said cartridge cleaner housing comprises a drain tube extending downwardly from said cleaning chamber into said disposal tank;

wherein said disposal tank is located beneath said cleaning chamber such that said spray-water from said at least one jet-spray nozzle drains downward into said disposal tank;

wherein said disposal tank is exteriorly attachable and alternately detachable to said cartridge cleaner housing;

wherein said disposal tank comprises a drain plug; and wherein said cartridge cleaner assembly is useful for cleaning said debris from between said multiple blades of said razor cartridge and extending a life span of said multiple blades of said razor cartridge.

19. The multiple blade razor cartridge cleaner system of claim 18 further comprising a kit including: at least one assembled said cartridge cleaner assembly having said clean water tank, said pump, said cartridge cleaner housing, said razor rest, said cleaning chamber having said spray cover, said at least one jet-spray nozzle, and said disposal tank; and at least one set of user instructions.

20. A method of using a multiple blade razor cartridge cleaner system of claim 1 comprising the steps of:

filling a clean water tank with a tap water;

beginning a shaving process;

placing a multiple blade razor cartridge on the top side of a cartridge cleaner housing;

activating the at least one jet-spray nozzle to clean said multiple blade razor cartridge as needed; and removing and storing said multiple blade razor cartridge.

* * * * *